United States Patent
Hamajima et al.

(10) Patent No.: US 6,326,525 B1
(45) Date of Patent: Dec. 4, 2001

(54) ABSORBENT ARTICLE WITH FREE EDGE PORTIONS

(75) Inventors: Mitsugu Hamajima; Masahito Tanaka; Yoji Kameo; Jinko Noguchi; Minoru Nakanishi; Hiroyuki Yokomatsu; Satoshi Tanaka, all of Tochigi-ken (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/063,051

(22) Filed: Apr. 21, 1998

(30) Foreign Application Priority Data

May 29, 1997 (JP) .................................................. 9-139875

(51) Int. Cl.[7] ...................................................... A61F 13/15
(52) U.S. Cl. .................... 604/378; 604/385.24; 604/387; 604/385.01
(58) Field of Search ................................ 604/385.2, 387, 604/385.1, 378, 385.01, 385.24

(56) References Cited

U.S. PATENT DOCUMENTS

| H1614 | 11/1996 | Mayer et al. |
|---|---|---|
| 4,029,101 | 6/1977 | Chesky et al. |
| 5,133,704 * | 7/1992 | Wheeler ................. 604/387 |
| 5,542,941 * | 8/1996 | Morita ................. 604/385.1 |
| 5,735,838 * | 4/1998 | Ronnberg et al. ........... 604/385.2 |
| 6,114,597 * | 9/2000 | Romare ....................... 604/378 |

FOREIGN PATENT DOCUMENTS

| 0604764 | 7/1994 | (EP) . |
|---|---|---|
| 64/12522 | 1/1989 | (JP) . |
| 8503638 | 4/1996 | (JP) . |
| 294501 | 1/1997 | (TW) . |
| WO 9412135 | 6/1994 | (WO) . |
| WO 9640029 | 12/1996 | (WO) . |
| WO 9709016 | 3/1997 | (WO) . |
| WO 9817217 | 4/1998 | (WO) . |

* cited by examiner

Primary Examiner—Dennis Ruhl
(74) Attorney, Agent, or Firm—Birch, Stewart, Kolasch & Birch, LLP (57) ABSTRACT

The present invention provides an absorbent article 1 having a substantially elongate configuration, comprising a liquid-impermeable leakage-preventive layer 3, and a liquid-retentive absorbent layer 2 disposed above the leakage-preventive layer 3, wherein the absorbent layer 2 comprises a liquid-retentive absorbent member 24 and a liquid-permeable topsheet 23, and is formed by a fixed portion 21 and one pair of left and right free edge portions 22, the fixed portion 21 being fixed to the leakage-preventive layer 3, the free edge portions 22 being located on opposite left and right sides in the longitudinal direction of the fixed portion 21 and each having a free end 22a, the absorbent member 24 being present in both of the fixed portion 21 and the pair of left and right free edge portions 22.

18 Claims, 9 Drawing Sheets

ABSORBENT ARTICLE WITH FREE EDGE PORTIONS

BACKGROUND OF THE INVENTION

This invention relates to an absorbent article such as a sanitary napkin, an incontinent pad, or the like, which has a nice fitness and a high leakage-preventive ability.

As an absorbent article, such as a sanitary napkin, an incontinent pad, or the like, there has heretofore been widely used a substantially vertically-long absorbent article including a liquid-retentive absorbent layer and a liquid-impermeable leakage-preventive layer.

Such an absorbent article is required to prevent leakage, particularly to effectively prevent leakage from the side portions, and many proposals have been made.

For example, in Japanese Utility Model Unexamined Publication (KOKAI) No. 1-2592, there is proposed a sanitary napkin, in which elastic members are arranged on both left and right side edge portions of an absorbent article so that a round-shaped configuration is exhibited on the body side of its user in a natural state.

In such a suggested sanitary napkin, however, the napkin, when in wear, tends to move together with the shorts in obedience to the motion of the wearer, and therefore, fitness is degraded and leakage occurs when slipped.

In Japanese Patent Unexamined Publication (KOKAI) No. 8-503638, there is proposed an absorbent article, in which cubic gathers comprising a topsheet, a backsheet, and an elastic member are provided on both left and right guide of an absorbent member such that the cubic gathers are erected.

Such a proposed sanitary napkin, however, cannot satisfy the required level of leakage-preventive ability and the leakage-preventive ability from the sides is degraded.

SUMMARY OF THE INVENTION

It is, therefore, an object of the present invention to provide an absorbent article, which has a nice fitness and a high leakage-preventive ability, and which is particularly capable of preventing leakage from the sides effectively.

As a result of search and development with a view to solving the above problems, the present inventors have found that the above object can be achieved by providing an absorbent article comprising a fixed portion forming an absorbent layer fixed to a leakage-preventive layer, and free edge portions each located on both left and right sides of the fixed portion and each having a free end.

The present invention provides an absorbent article having a substantially elongate configuration, comprising a liquid-impermeable leakage-preventive layer, and a liquid-retentive absorbent layer disposed above the leakage-preventive layer, wherein the absorbent layer comprises a liquid-retentive absorbent member and a liquid-permeable topsheet, and is formed by a fixed portion and one pair of left and right free edge portions, the fixed portion being fixed to the leakage-preventive layer, the free edge portions being located on opposite left and right sides in the longitudinal direction of the fixed portion and each having a free end, the absorbent member being present in both of the fixed portion and the pair of left and right free edge portions.

The absorbent article according to the present invention has a nice fitness and a high leakage-preventive ability, and is particularly capable of effectively preventing leakage from the sides.

DESCRIPTION OF THE PREFERRED EMBODIMENTS

An absorbent article according to the present invention will be described hereinafter in detail with reference to the drawings.

Figure 1:
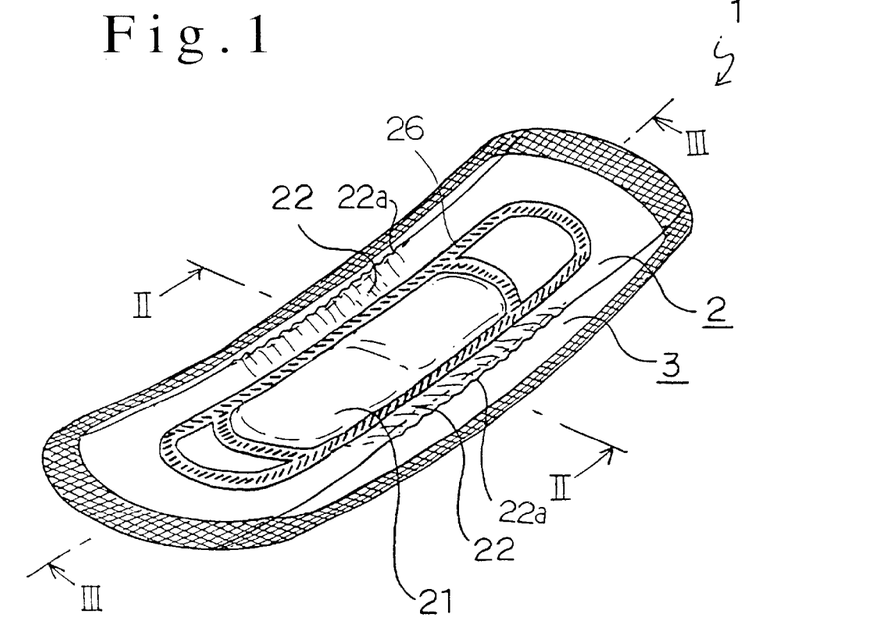
FIG. 1 is a perspective view showing one embodiment of an absorbent article of the present invention.
Figure 2A:
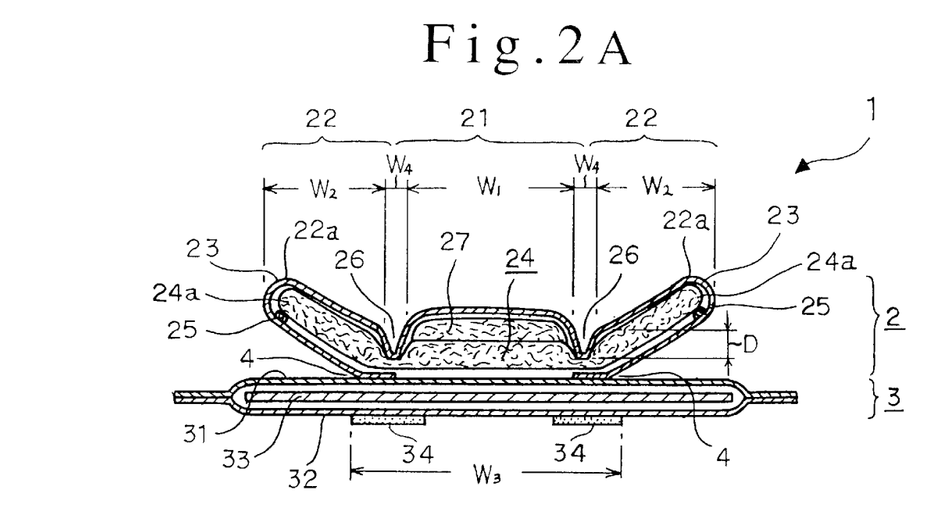
FIG. 2A is a sectional view taken on II—II of FIG. 1.
Figure 2B:
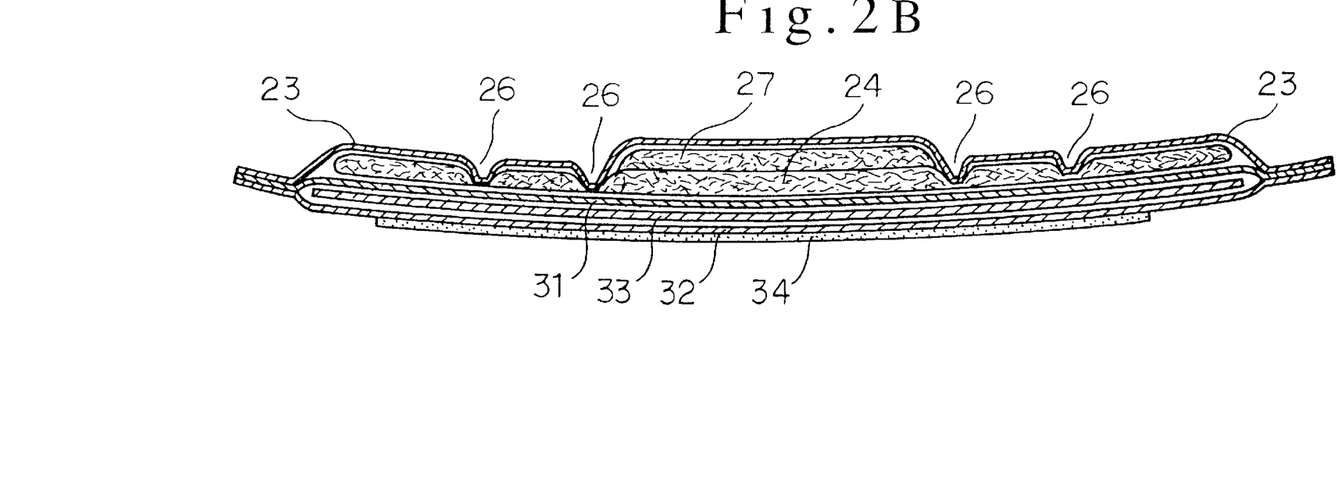
FIG. 2B is a sectional view taken on line III—III of FIG. 1.

Here, FIG. 1 is a perspective view showing a sanitary napkin as the first embodiment of an absorbent article according to the present invention, FIG. 2A is a sectional view taken on II—II of FIG. 1, and FIG. 2B is a sectional view taken on line III—III of FIG. 1.

A sanitary napkin 1 according to the first embodiment shown in FIGS. 1, 2A, and 2B has a substantially elongate configuration, including a liquid-retentive absorbent layer 2, and a liquid-impermeable leakage-preventive layer 3. When in use, the napkin 1 is attached to an undergarment.

In the sanitary napkin 1 according to this embodiment, the absorbent layer 2 comprises a liquid-retentive absorbent member 24 and a liquid-permeable topsheet 23, and is formed by a fixed portion 21 fixed to the leakage-preventive layer 3 and one pair of left and right free edge portions 22 located on opposite left and right sides in the longitudinal direction of the fixed portion 21 and each having a free end 22a, the absorbent member 24 being present in not only the fixed portion 21 but also in the pair of left and right free edge portions 22.

When the sanitary napkin 1 according to this embodiment is used, the leakage-preventive layer 3 moves directly in obedience to the motion of an undergarment, but the one pair of free end portions 22 on the absorbent layer 2 do not move directly in obedience to the motion of the undergarment.

More specifically, the free edge portions 22 have each an elastic member 25 arranged over a predetermined length along a longitudinal direction of the absorbent layer 2, the free edge portions 22 being erected towards a skin contacting surface side by contraction of the elastic member 25. The expression "erected" used herein refers not only to an upright state but also to an upwardly floated state from the leakage-preventive layer.

The topsheet 23 is arranged in such a manner as to cover at least the skin contacting surface side of the absorbent member 24, the fixed portion 21 is located on a widthwise central portion of the absorbent layer 2, and the one pair of free edge portions 22 are continuous with opposite left and right side edges of the fixed portion 21, respectively. The term "continuous" used herein refers to a state that the side edge of the fixed portion 21 and the side edges of the free edge portions 22 are continuous with each other.

As shown in FIGS. 2A and 2B, the absorbent layer 2 comprises the absorbent member 24, and the topsheet 23 provided in such a manner as to cover an outer surface and side surfaces of the absorbent member 24 and back surfaces (the portion not contacting the leakage-preventive layer 3) of the free edge portions 22. Owing to this arrangement, the absorbent member 24 is present over the widthwise entire area of the absorbent layer 2. In the absorbent layer 2, a second absorbent layer 27 is disposed on the fixed portion 21 between the topsheet 23 and the absorbent member 24.

As shown in FIG. 2, the leakage-preventive layer 3 comprises a liquid-permeable sheet 31, a leakage-preventive sheet 32, and an absorptive portion 33 interposed therebetween. That is, as shown in FIG. 2, in the leakage-preventive layer 3, the absorptive portion 33 consisting of an absorbent sheet(s) is held between the liquid-permeable sheet 31 and the leakage-preventive sheet 32, and the liquid-permeable sheet 31 and the leakage-preventive sheet 32 are sealed at a peripheral edge portion of the absorptive portion 33.

The absorbent layer 2 is placed on the liquid-permeable sheet 31 of the leakage-preventive layer 3 and fixed by bonding thereto through an adhesive agent 4 applied to opposite left and right side edge portions of the fixed portion 21. Longitudinal opposite end edges of the absorbent layer 2 and the leakage-preventing layer 3 are fixed by heat sealing.

The width W1 of the fixed portion 21 is preferably 15 to 60 mm. The width W2 of the free edge portions 22 is preferably 5 to 30 mm.

The elastic member 25 is disposed generally over entire area in the longitudinal direction of the absorbent member 24 along the opposite left and right side edge portions 24a, 24a of the absorbent member 24, on the back surface side of the absorbent member 24 at the fee ends 22a of the free edge portions 22.

As a material forming the elastic members 25, 25, a film, a fiber, a foamed body and the like composed of a polymer of a number of rubbers, such as polyurethanes, polybutadiene, isoprene and the like, ethylene-vinyl acetate, and a number of polyolelins having extensibility can be used. In order to obtain favorable effects (desired effects of the present invention) without degrading the comfortable wearing perception, the elastic members 25, 25 are preferably 10 to 300 gf in stress at 30% expansion.

The predetermined length for the arrangement of the elastic members 25, 25 is not particularly limited. In order to erect the free edge portions 22, 22 into a configuration nicely fitted to the wearer, the elastic member 25, 25 are disposed preferably over the length of 15 to 90% of the entire length of the sanitary napkin 1, and more preferably over the length of 50 to 90%.

The leakage-preventive layer 3 is provided on a back surface side thereof with a slip-preventive means 34 for attaching the sanitary napkin to an objective member to be attached such as an undergarment when in use. The width W3 of the sanitary napkin fixed by the slip-preventive means 34 is preferably larger than the width W1 of the fixed portion 21 of the absorbent layer 2 because in doing so, the leakage-preventive layer becomes easier to move in obedience to the motion of the undergarment. The slip-preventive means is not particularly limited inasmuch as it is usually used, such as a double faced adhesive tape, a hot-melt adhesive agent, a mechanical hook, or the like. In this embodiment, a hot-melt agent is applied so as to be used as the slip-preventive means.

In this embodiment, two straps of the slip preventive means 34 are provided on the side of opposite left and right side edges in the longitudinal direction of the sanitary napkin 1. The width W3 refers to the width between the outer edges of the two straps of the slip preventive means 34, 34. In case two or more straps of the slip preventive means 34 are provided, the space between adjacent slip preventive means 34, 34 is fixed. In such a case, therefore, the space between the adjacent slip preventive means is included as the "width of the fixed portion".

The width W3 of the slip preventive means shown in FIG. 2 is preferably 30 to 80 mm. In case the sanitary napkin is of the type having wings including flaps extending to the longitudinal opposite sides thereof, it is likewise preferred that the slip preventive means 34 is provided on the leakage-preventive layer 3 about the fixed portion. The slip-preventive means 34 may be provided on a wing fixing portion which is provided on the backsheet side of the wing portions. This width (a space between an external and an external of the spread flaps prior to be worn) is the "width of the portion to be fixed", i.e., the width W3. In this case, the width W3 is preferably 100 to 180 mm.

In order to erect the free edge portions 22 in a more favorable fashion, as shown in FIGS. 1 and 2, groove portions 26 are formed in the opposite left and right side edges on the opposite left and right side portions of the fixed portion 21. The depth D of each groove portion 26 is preferably 0.1 to 5 mm. The width W4 of each groove portion 26 is preferably 0.1 to 5 mm.

As shown in FIG. 1, each groove portion 26 including the side edge of the fixed portion 21 is formed into a configuration similar to an outer peripheral configuration of the sanitary napkin 1. On the side edge sides of the fixed portion 21, the fixed portion 21 and the free edge portions 22 are divided by the groove portion 26.

Owing to a provision of the groove portions 26, a body fluid is more effectively prevented from dispersing and the groove portions 26 also act as flexible axes to make it easier for the free edge portions to be erected upwardly.

The material, etc. of each member constituting the sanitary napkin will be described next.

As a material of the topsheet 23, there is no particular limitation in as much as the material is usually used as the topsheet of an absorbent article such as a sanitary napkin, or the like. For example, the desired material includes a nonwoven fabric composed of a synthetic fiber, such as polyethylene fiber, polypropylene fiber polyester fiber, polyethylene/polypropylene conjugate fiber, polyethylene. polypropylene conjugate fiber, an apertured film obtained by aperturing such film as polyethylene, or the like. Among all, apertured nonwoven fabric, apertured polyethylene film, or the like which is subjected to aperturing treatment in order to enhance absorption is particularly preferable in view of absorption.

As a material of the absorbent member 24, an absorbent sheet and a polymer sheet can be listed. The thickness of the absorbent member 24 is preferably 0.3 to 5 mm.

As such an absorbent sheet and a polymer sheet, one usually used as an absorbent article such as a sanitary napkin can be used without any particular limitation.

The absorbent sheet particularly preferably used in the present invention can be absorbent paper nonwoven fabric, a pulp sheet made of fibers and a binder, or the like. The polymer sheet can be a sheet made of a mixture of fluff pulp and fiber With a superabsorbent polymer. The sheet made of a mixture of fiber and a superabsorbent polymer may be a superabsorbent polymer in the sheet dispersed either in layers or in three dimensions.

A material for forming the absorbent sheet and a fiber used in the polymer sheet preferably includes cellulose fiber, such as wood pulp; regenerated cellulose fiber, such as viscous rayon and cuprammonium rayon, synthetic hydrophilic fiber, such as polyvinyl alcohol fiber and polyacrylonitrile fiber, and synthetic fiber with the surface thereof rendered hydrophilic with a surface active agent, etc. such as polyethylene fiber, polypropylene fiber, polyethylene terephthalate fiber. polyethylene/polypropylene conjugate fiber, and polyethylene/polyethylene terephthalate conjugate fiber. Cellulose fibers are preferred for their satisfactory retention of hydrophilic properties.

The superabsorbent polymer which can be used in the polymer sheet is preferably the one capable of absorbing and retaining 20 or more times as much liquid as its own weight and gelling upon liquid absorption. Such superabsorbent polymers include starch, crosslinked carboxymethylated cellulose, polyacrylic acid or a salt thereof, and a polyacrylic acid salt graft polymer. The polyacrylic acid salt is preferably sodium polyacrylate. Acrylic acid copolymers containing a comonomer, such as maleic acid, itaconic acid, acrylamide, 2-acrylamide-2-methylpropanesulfonic acid, 2-(meth)acryloylethanesulfonic acid, 2-hydroxyethyl (meth) acrylate or styrenesulfonic acid, in such a proportion that does not impair its performance as a superabsorbent polymer, can also be preferably used.

It is particularly preferable to use superabsorbent polymers capable of absorbing and retaining a large quantity of liquid through ionic osmosis and yet having no leaks even under pressure, comprising water-insoluble and hydrophilic crosslinked polymer particles which are obtained by polymerizing acrylic acid or an alkali salt thereof (e.g. sodium or potassium), etc. followed by crosslinking for water insolubilization.

A preferred polymer sheet among the above-mentioned polymer sheets is the one made up of a hydrophilic fiber, a thermally fusible bonding fiber or a strengthening assistant, and a superabsorbent polymer. The superabsorbent polymer is not present on the absorbent surface of the polymer sheet for absorbing liquid but distributed inside the polymer sheet, and adhered to the hydrophilic fiber constituting the polymer sheet and hardened. The superabsorbent polymer is spread in an amount of 5 to 300 g/m2 of the polymer sheet and the polymer sheet has a thickness of 0.3 to 1.5 mm.

In such a polymer sheet, since a superabsorbent polymer is fixedly dispersed in a single sheet in a three-dimensional pattern, the absorption ability of the superabsorbent polymer is effectively exhibited. Moreover, the gel blocking of the superabsorbent polymer is less. Accordingly, a body fluid tends to pass through the absorbent sheet smoothly. Thus, the absorbent sheet can advantageously be used in order to obtain a high absorption ability.

In the present invention, from a view point of high absorption ability of body fluid, the polymer sheet is preferably used. Also, the absorbent sheet and the polymer sheet overlaid one upon the other in superimposed relation may be used. When they are overlaid, the polymer sheet is preferably located on the lower layer side, i.e., leakage-preventive layer 3 side.

As the liquid-permeable sheet 31 forming the leakage-preventive layer 3, the leakage-preventive sheet 32 and the absorbent sheet as the absorptive portion 33, the elastic member 25, an adhesive agent 4 for fixing the absorbent layer 2 and the leakage-preventive layer 3, and a viscous agent forming the slip-preventive means 34, those usually used in an absorbent article such as a sanitary napkin can be used without any particular limitation.

In the sanitary napkin 1 thus constructed according to this embodiment, when in use, the leakage-preventive layer 3 is attached to an undergarment such as the shorts through the slip-preventive means 34. And, as previously mentioned, the absorbent layer 2 is not fixed directly to the undergarment but only through the leakage-preventive layer 3 Accordingly, when the wearer moves, the leakage-preventive layer 3 moves in obedient to the motion of the undergarment but the opposite left and right free edge portions 22 of the absorbent layer 2 do not move directly in obedient thereto. Thus, the effect from the motion of the wearer is less. Accordingly, the absorbent layer 2 is not easily slipped and a nice fitness can be obtained. Moreover, since the absorbent member 24 is situated up to the side edges of the absorbent layer 2 and there is a provision of the elastic member, the absorbent layer 2 can be retained normally in a nicely fitted state to the wearer's body. Since no gap is formed and the menses can be absorbed, leakage from the sides can be prevented particularly effectively.

According to the sanitary napkin 1 of this embodiment, even if a discharged body fluid migrates widthwise sidewardly beyond or passing through the free edge portions 22 of the absorbent layer 2, leakage from the sides can effectively prevented by the leakage-preventive layer 3 located outside of the free edge portions 22. Particularly, in case the width of the slip-preventive means 34 is set larger than the width of the fixed portion 21, the leakage-preventive layer 3 moves in obedience with the motion of the undergarment and fully covers the lower surface of the absorbent layer, and therefore, particularly effective.

Furthermore, in the construction of this embodiment, in case the present invention is applied to an absorbent article such as a disposable diaper, an incontinent pad, or the like in which a large quantity of body fluid is discharged, there can easily be employed such a suitable countermeasure as that the absorbent portion 33 in the leakage-preventive layer 3 contains the superabsorbent polymer.

The sanitary napkin according to this embodiment can be manufactured by forming the absorbent layer 2 and the leakage-preventive layer 3 in accordance with the normal procedure and thereafter, affixing them using the adhesive agent 4. The layers 2 and 3 may be affixed at the same time the groove portion is formed. In the alternative, after the groove portion is formed, the absorbent layer 2 formed with the groove portion may be fixed to the leakage-preventive layer 3.

Another embodiment of an absorbent article of the present invention will now be described with reference to FIG. 3.

Figure 3:
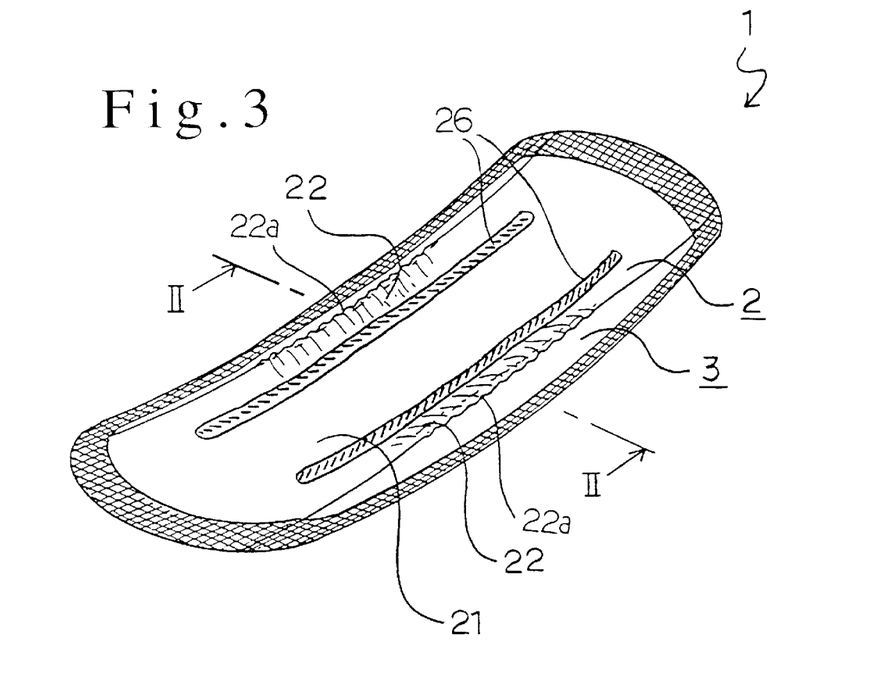
FIG. 3 is a sectional perspective view showing another embodiment of an absorbent article of the present invention.

Here, FIG. 3 is a perspective view showing another embodiment of an absorbent article of the present invention.

In the sanitary napkin 1 according to the second embodiment shown in FIG. 3 the configuration of the groove portions 26 is linear. The remaining construction is the same as the first embodiment. Although, there is no provision of the second absorbent member, this may be provided, where necessary.

As discussed, the configuration of the groove portions 26 is not particularly limited but can be selected as desired.

Since a sectional view taken on line II—II of the sanitary napkin shown in FIG. 3 is the same as FIG. 2, an illustration thereof is omitted.

In the first and second embodiments, the fixed portion and the free edge portions are formed from a single absorbent member and a single topsheet, respectively. Other examples, in which the fixed portion and the free edge portions are formed from separately formed two or more absorbent members, will now be described with reference to FIGS. 4 to 7.

Here, FIGS. 4 to 7 are sectional perspective views showing other embodiments of an absorbent article of the present invention, respectively (perspective views showing the state taken in a widthwise direction at its longitudinal, central portion of the absorbent article).

In the description to follow, the component members identical or similar to those of the first embodiment are denoted by identical reference numerals plus 100, respectively and only those points different from the first embodiment are particularly described. The points not particularly described are the same as the first embodiment.

Figure 4:
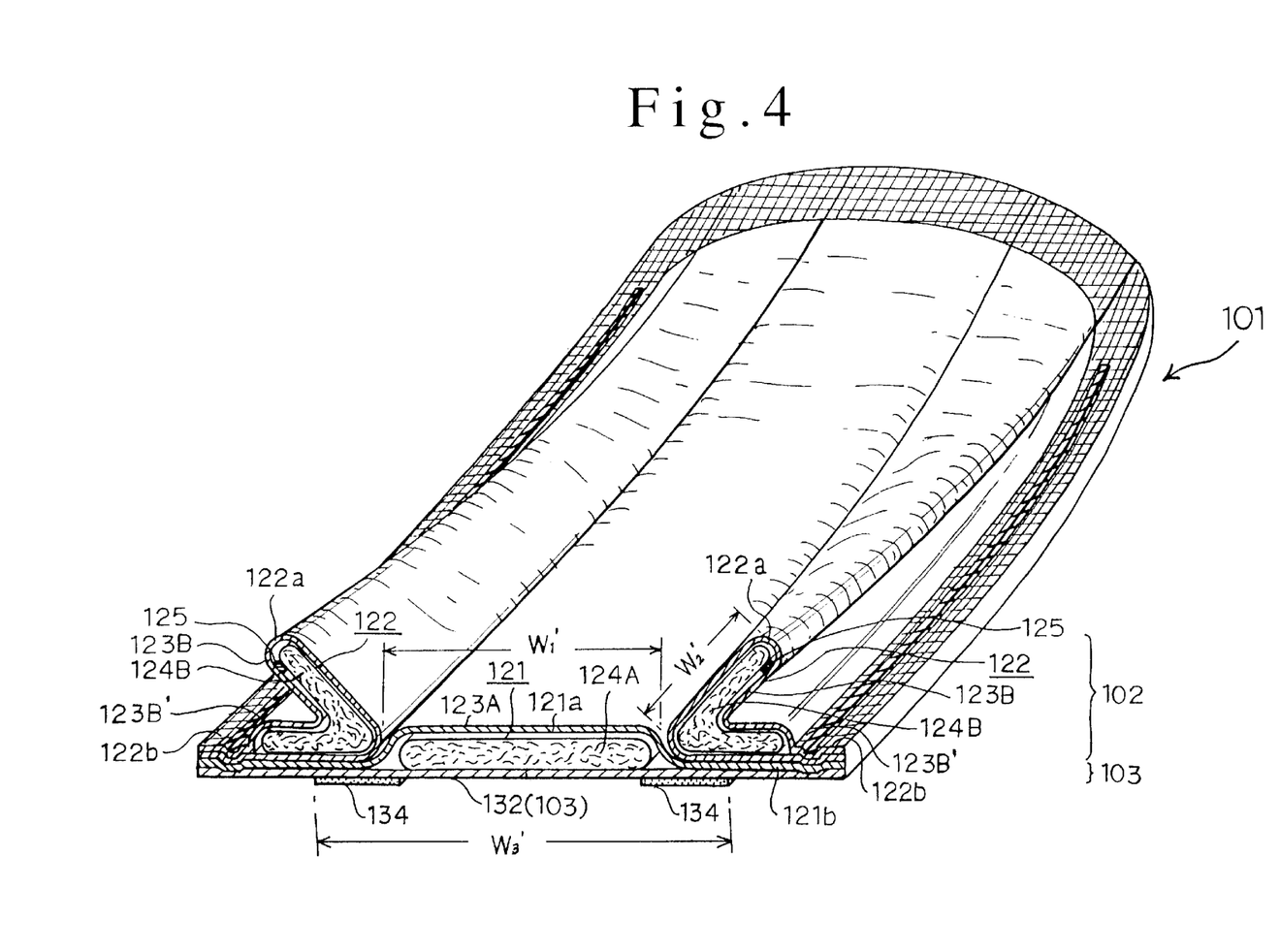
FIG. 4 is a sectional perspective view showing a further embodiment of an absorbent article of the present invention.

In a sanitary napkin 101 according to the third embodiment shown in FIG. 4, a fixed portion 121 comprises a fixed portion topsheet 123A provided in such a manner as to cover the outer surface side of the fixed portion absorbent member 124A. The free edge portions 122 each comprise a free edge portion topsheet 123B provided in such a manner as to cover the outer surface of the free edge portion absorbent member 124B. The free edge portions 122 are firmly secured at basal end portions 122b thereof to opposite left and right side portions of the fixed portion 121.

More specifically, in this embodiment, the leakage-preventive layer 103 comprises only a leakage-preventive sheet 132.

The fixed portion absorbent member 124A exhibits a rectangular configuration (not shown) and is provided on a widthwise central portion of the sanitary napkin. The fixed portion topsheet 123A is provided in such a manner as to cover the outer surface side and the side surfaces side of the fixed portion absorbent member 124A and also cover the widthwise entire surface of the leakage-preventive sheet 103.

Each free edge portion 122 comprises a free edge portion topsheet 123B provided in such a manner as to cover the outer surface of a strip-shaped free edge portion absorbent member 124B. The free edge portions 122 are fixed to the fixed portion 121 by heat sealing basal end portions 122b contacted by opposite side edges 123B' to side edge portions 121b (where the fixed portion absorbent member 124A is not present but only the fixed portion topsheet 123A is present) of the fixed portion 121. The free edge portions 122 are also integral with the leakage-preventive layer 103.

The free edge portions 122 are folded back widthwise outwardly of the sanitary napkin 101 at its part adjacent to the fixed portion absorbent member 124A on the basal end portions 122b side.

The elastic member 125 is provided on the back surface side of the free edge portion absorbent member 124B at the free ends 122a of the free edge portions 122.

The width W2' of those portions of the free edge portions 122 which are folded back and erected is preferably 5 to 30 mm, and the width W1' of the central portion 121a (where the fixed portion absorbent member 124A is provided) of the fixed portion 121 is preferably 15 to 60 mm. The width W1' of the central portion 121a is smaller than the width W3' of the sanitary napkin fixed by the slip-preventive means 134.

As the fixed portion absorbent member 124A, the fixed portion topsheet 123 A, the free edge portion absorbent member 124B, the free edge portion topsheet 123B, the leakage-preventive sheet 132, etc., the absorbent member, the top sheet, the leakage-preventive sheet, etc. which were described in detail in the first embodiment may be used without any particular limitation.

Also in the sanitary napkin 101 thus constructed according to this embodiment, the absorbent article can be fixed in use to the undergarment as in the same manner as the first embodiment and the leakage-preventive layer likewise moves in obedient to the motion of the undergarment but the free edge portions (particularly the erected portions) do not move directly in obedience to the motion of the undergarment, and the same effects can be exhibited. The sanitary napkin 101 according to this embodiment can be manufactured by forming the fixed portion 121 by fixing the fixed portion absorbent member 124A and the fixed portion topsheet 123A to the leakage-preventive layer 103 comprising the leakage-preventive sheet 132 using an adhesive agent, or the like, and then fixing the free edge portions 122 to the fixed portion 121 by heat sealing.

An absorbent article according to the fourth to sixth embodiment shown in FIGS. 5 to 7 will now be described. In the description to follow, those points different from the third embodiment are particularly described in detail. The points not particularly described are the same as the third embodiment.

Figure 5:
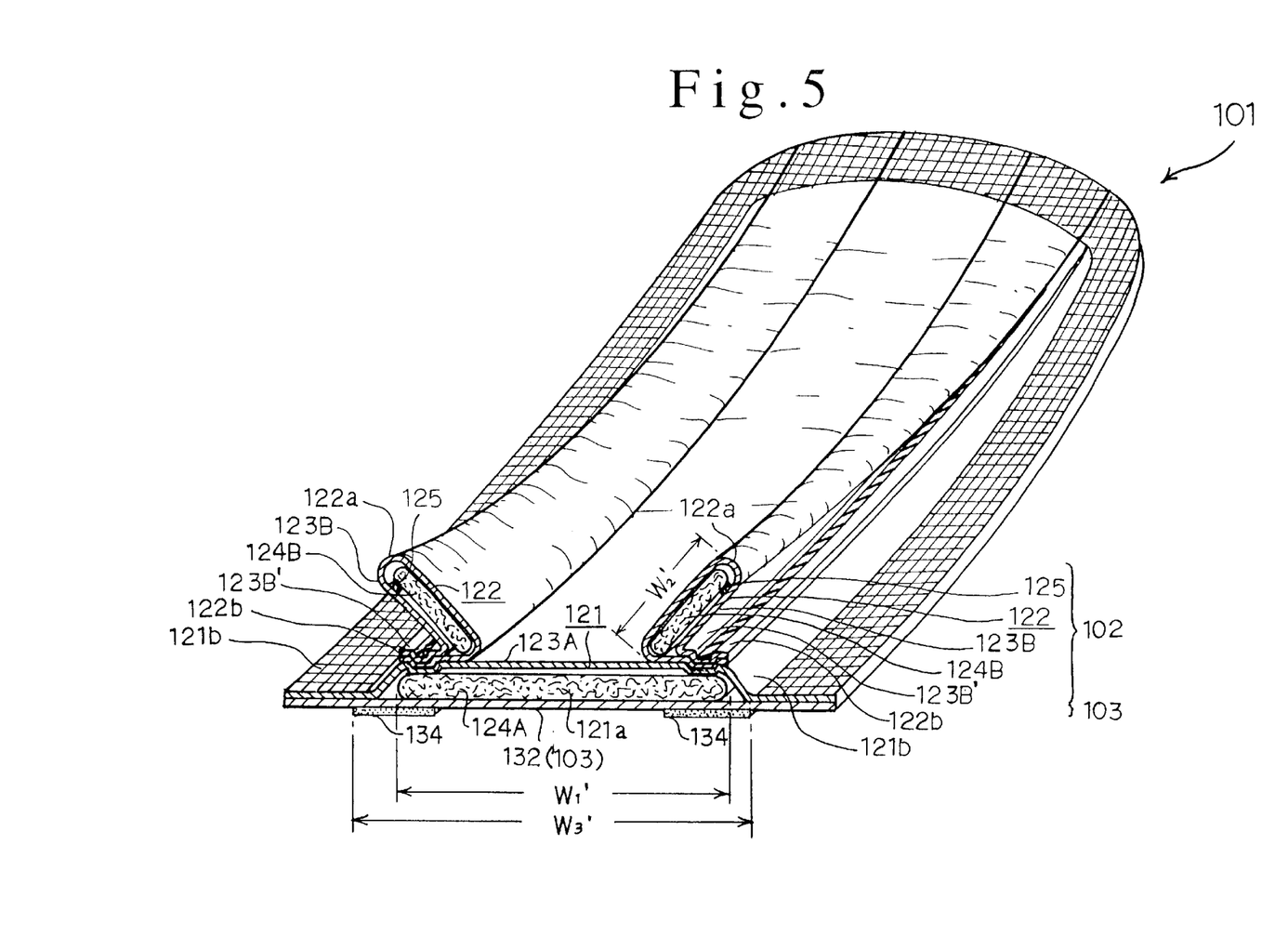
FIG. 5 is a sectional perspective view showing a still further embodiment of an absorbent article of the present invention.

In the sanitary napkin 101 according to the fourth embodiment shown in FIG. 5, the basal end portions 122b of the free edge portions 122 are firmly secured to the fixed portion 121.

More specifically, in this embodiment, the free edge portions 122 are fixed to the fixed portion 121 by heat sealing the basal end portions 122b contacted by the opposite side edges 123B' of the free edge portion topsheet 123B to side edge portions of that portion of the fixed portion 121 where the fixed portion absorbent member 124A is present.

The free edge portions 122 are folded back widthwise outwardly on the basal end portion 122b side.

Figure 6:
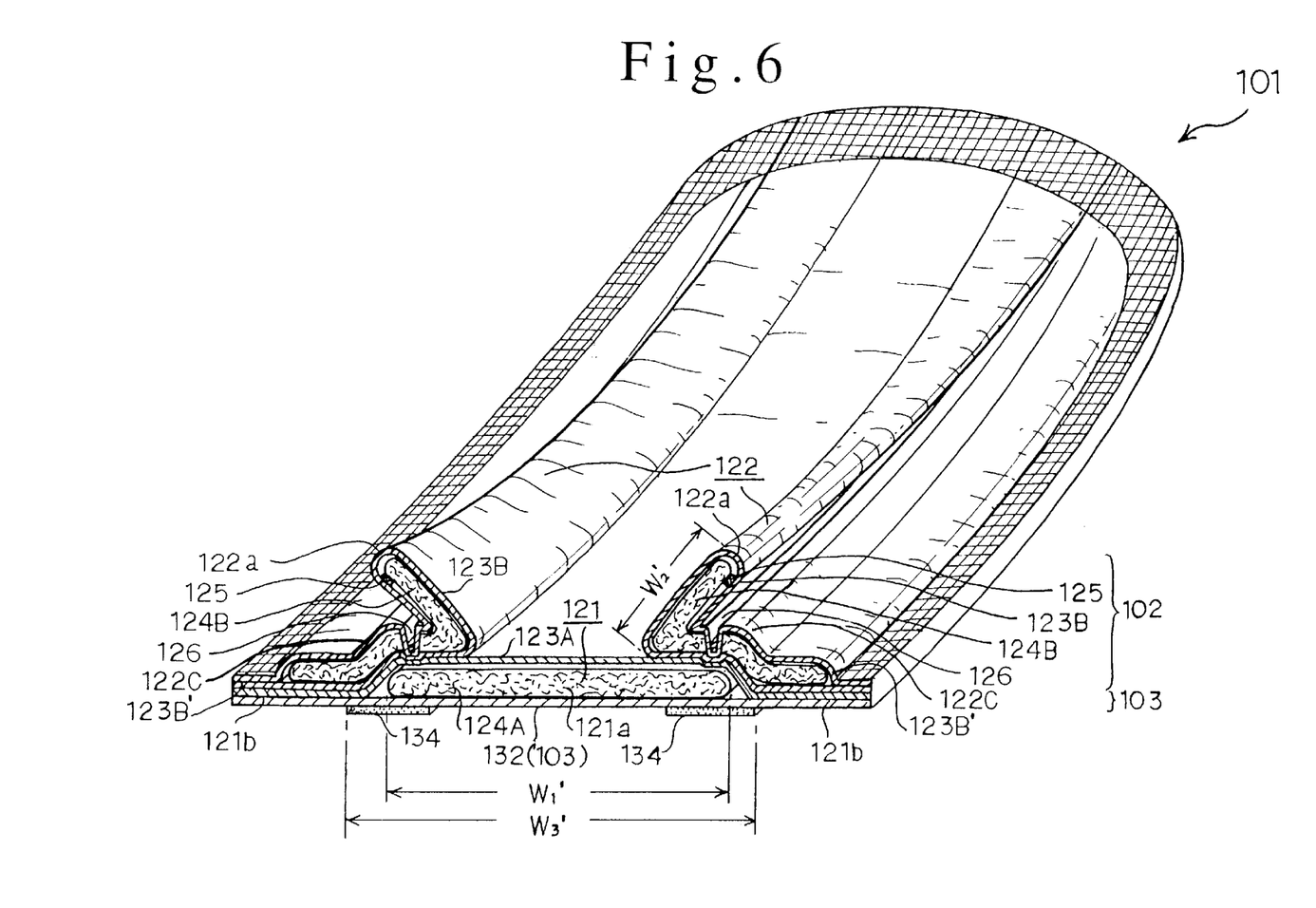
FIG. 6 is a sectional perspective view showing a yet further embodiment of an absorbent article of the present invention.

In the sanitary napkin 101 according to the fifth embodiment shown in FIG. 6, the free edge portions 122 are firmly secured at intermediate portions 122C thereof to the fixed portion 121.

More specifically, in this embodiment, the free edge portions 122 are such that the basal end portions 122b contacted by the opposite side edges 123B' of the free edge portion topsheet 123B are located on the side edge portions 121b (where the fixed portion absorbent member 124A is not present but only the fixed portion topsheet 123A is present) of the fixed portion 121, and the free ends 122a are located above the side edge portions in such a manner as to cover the side surfaces and the outer surface side of the side edge portions of the fixed portion absorbent member 124A. The free edge portions 122 are firmly secured to the fixed portion 121 by heat sealing such that groove portions 126 are formed in the intermediate portions 122C of the free edge portions 122, i.e., those portions of the fixed portion absorbent member 124A which are located on the outer surface side of the side edge portions.

The free edge portions 122 are folded back widthwise outwardly of the sanitary napkin on the center side in the intermediate portions 122C.

Figure 7:
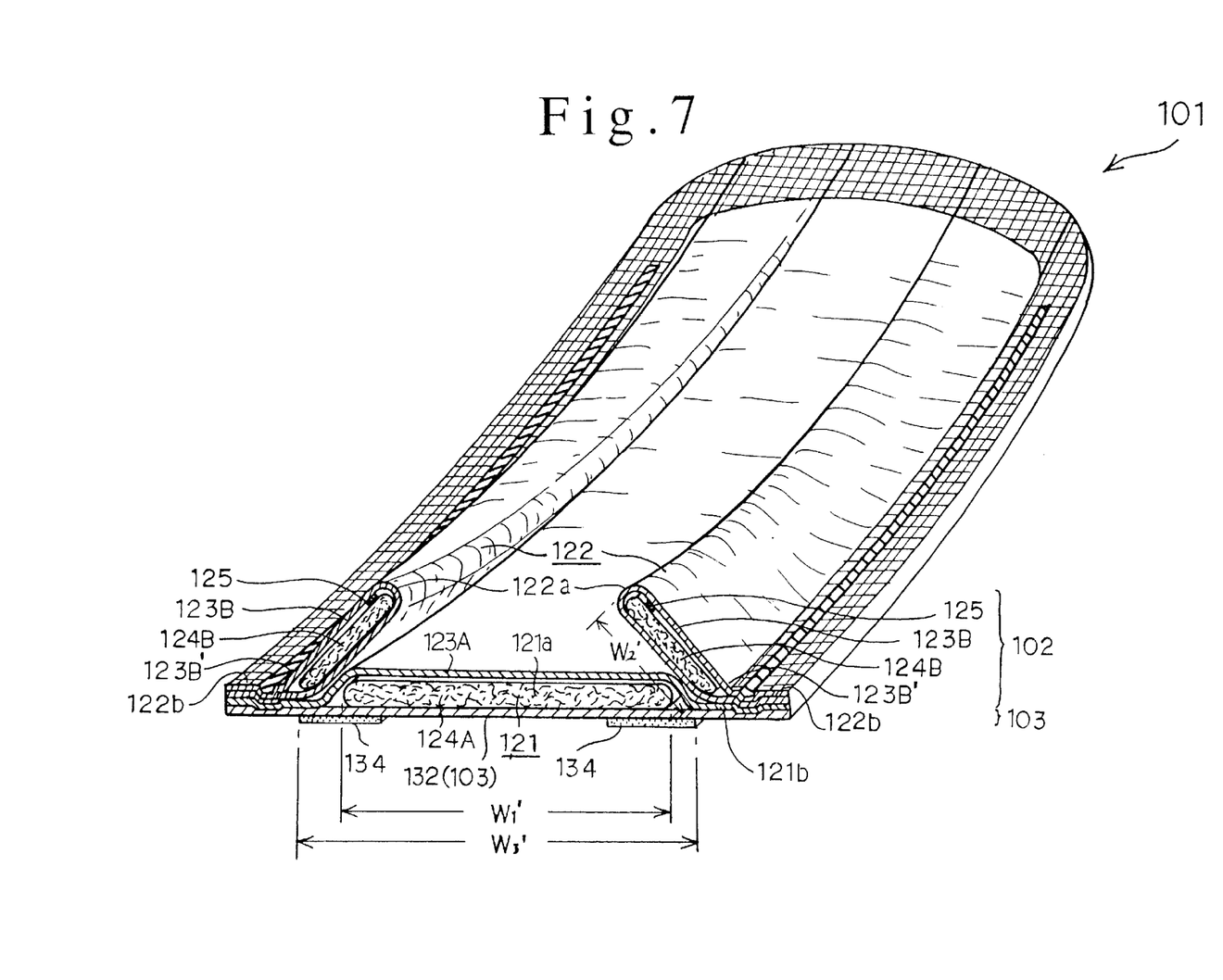
FIG. 7 is a sectional view showing an additional embodiment of an absorbent article of the present invention.

In the sanitary napkin 101 according to the sixth embodiment shown in FIG. 7, the free edge portions 122 firmly secured at the basal end portions 122b thereof to the fixed portion 121.

More specifically, in this embodiment, the free edge portion is 122 are not folded back but are erected upwardly above the fixed portion absorbent member 124A.

Also in those fourth to sixth embodiments, the absorbent article can be used in the same manner as the third embodiment, and the same functions and effects can be exhibited.

Further embodiments of the present invention will be described hereinafter in more detail with reference to the drawings.

Figure 8:
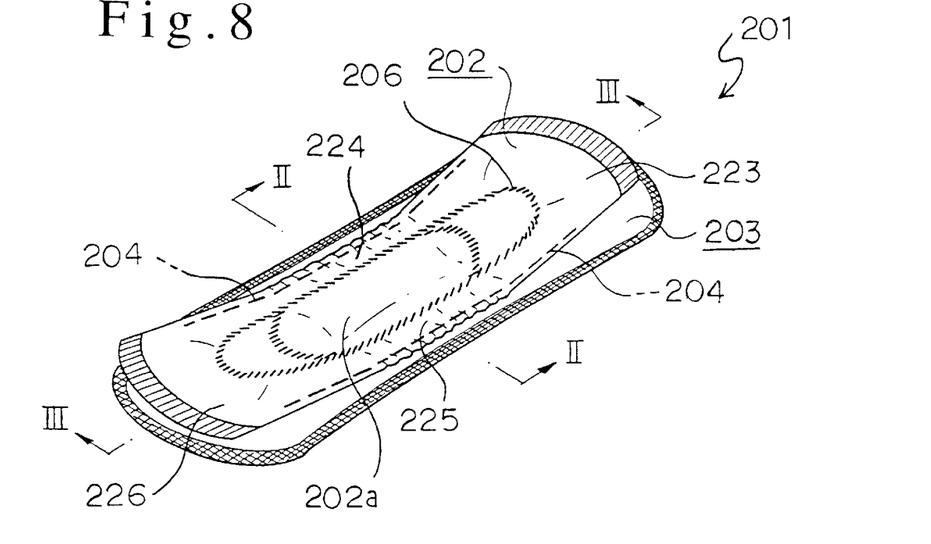
FIG. 8 is a perspective view showing a sanitary napkin as the seventh embodiment of an absorbent article of the present invention.
Figure 9:
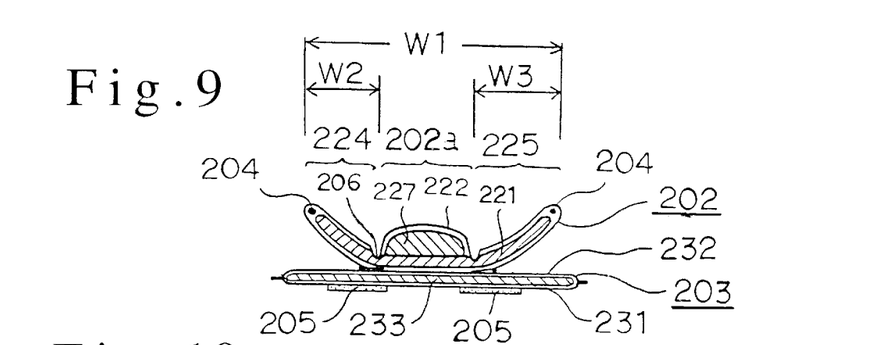
FIG. 9 is a sectional view taken on line II—II of the sanitary napkin shown in FIG. 8.
Figure 10:
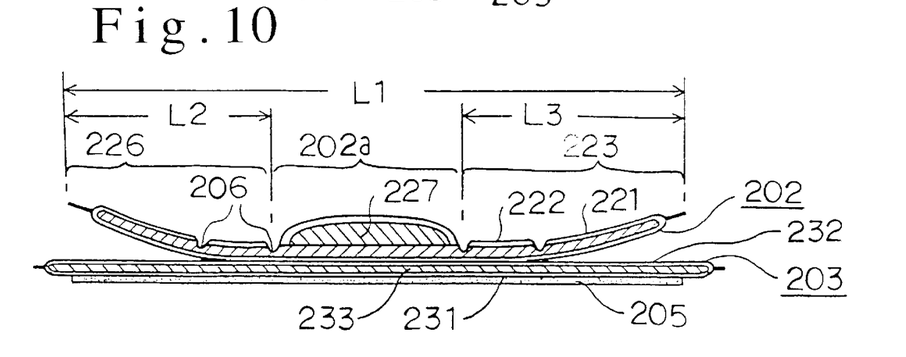
FIG. 10 is a sectional view taken on line III—III of the sanitary napkin shown in FIG. 8.
Figure 11:
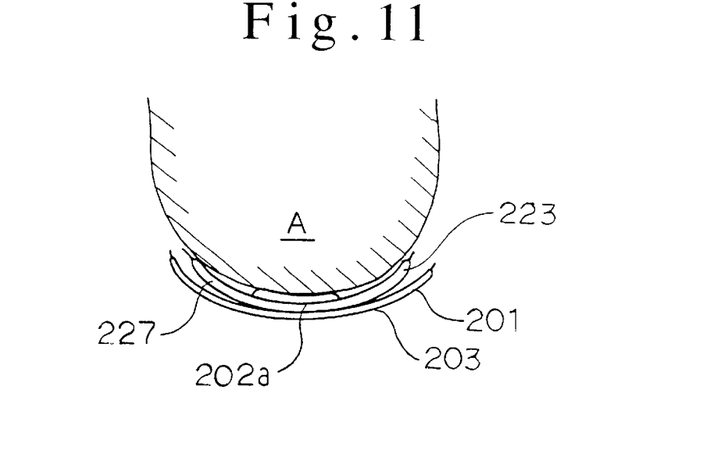
FIG. 11 is a schematic view showing a state of use of the sanitary napkin shown in FIG. 8.

Here, FIG. 8 is a perspective view showing a sanitary napkin as the seventh embodiment of the absorbent article of the present invention, FIG. 9 is a sectional view taken on line II—II of the sanitary napkin shown in FIG. 8, FIG. 10 is a sectional view taken on line III—III of the sanitary napkin shown in FIG. 8, and FIG. 11 is a schematic view showing a state of used of the sanitary napkin shown in FIG. 8.

In the description to follow, those points different from the first embodiment are particularly described. The points not particularly described are the same as the first embodiment, and the same functions and same effects can be exhibited.

As shown in FIG. 8, a sanitary napkin 201 as the absorbent article of this embodiment includes a liquid-impermeable leakage-preventive layer 203, and a liquid-retentive absorbent layer 202 provided above the leakage-preventive layer 203. This napkin 201 is formed substantially in a vertically long configuration.

In the sanitary napkin 201 according to this embodiment, as shown in FIGS. 8 to 10, the absorbent layer 202 includes a liquid-retentive absorbent member 221, and a liquid-permeable topsheet 222 provided in such a manner as to cover an entire surface (skin contacting surface side and back surface side) of the absorbent member 221. On the absorbent layer 202, a fixed portion 220a formed by fixing a longitudinal central portion 202a of the absorbent layer to the leakage-preventive layer 203, and a rear free edge portion 223 where the leakage-preventive layer 203 is not fixed are formed. An elastic member 204 is disposed at least on the rear edge portion 223 over a predetermined length along the longitudinal direction of the absorbent member 221, such that the rear free edge portion 223 is erected upwardly of the leakage-preventive layer 203 by contraction of the elastic member 204.

More specifically, in the sanitary napkin 1 according to this embodiment, as shown in FIGS. 8 to 10, only the central portion 202a is firmly secured to the leakage-preventive layer 203, and a front fee edge portion 226 is formed thereon together with the rear free edge portion 223. An elastic member 204 is disposed on the front free edge portion 226, so that the front free edge portion 226 is erected upwardly of the leakage-preventive layer 203 by contraction of the elastic member 204.

A left free edge portion 224 and a right free edge portion 225 are formed on opposite left and right sides of the central portion 202a, respectively. The elastic members 204 are disposed on the left free edge portion 224 and the right free edge portion 225 over a predetermined length along the longitudinal direction of the absorbent member 221, so that the elastic members 204 are erected upwardly of the leakage-preventive layer 203.

In this way, the front free edge portion 226, the rear free edge portion 223, the left free edge portion 224, and the right free edge portion 225 are formed, such that they are erected upwardly under the effect of the elastic member. As a consequence, the absorbent layer 202 is curved to exhibit a cup-like configuration as a whole.

In order to erect the front, rear, left, and right free edge portions 226, 223, 224, 225 in the absorbent layer 202 in a more favorable fashion so that a cup-like configuration having a nice fitness can be formed, as shown in FIG. 8, a groove portion 206 is formed in the absorbent layer 202. Within the groove portion 206, a second absorbent member 227 is placed on the absorbent member 221, thereby forming a cubic configuration.

As shown in FIGS. 9 and 10, the leakage-preventive layer 203 comprises a liquid-permeable sheet 232, a leakage-preventive sheet 231, and an absorbent sheet 233 interposed therebetween.

As shown in FIGS. 8 to 10, the elastic members 204 are disposed on the opposite left and right side edges in the longitudinal direction of the absorbent layer along the edge portion of the absorbent member 221. The elastic members 204 are covered with the topsheet 222 and bonded to the topsheet through an adhesive agent (not shown). The length of each elastic member 204 is preferably 40 to 90 when the length of the absorbent layer is set to 100.

It should be noted that the terms "front", "left", "right", and "rear" are used for the sake of convenience in this specification, and those words are not intended to define the direction of attachment unless particularly defined otherwise.

The width W1 of the absorbent layer is preferably 30 to 100 mm, and the length L1 thereof is preferably 150 to 350 mm.

The longitudinal curvature (radius of curvature) of the absorbent layer 202 is preferably 60 to 250 mm, and the widthwise curvature (radius of curvature) thereof is preferably 30 to 100 mm. This radius of curvature can be obtained as follows.

[How to Obtain the Radius of Curvature]

Figure 15A:
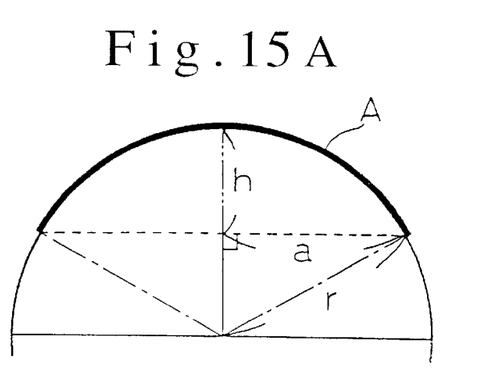
FIG. 15A and FIG. 15B are a schematic view schematically showing a method for measuring a radius of curvature.

A circular arc A shown in FIG. 15A has a curvature =1/radius of curvature (r). The radius of curvature (r) is expressed by the following equation ① in accordance with the third power theorem.

$$(r-h)^2 + a^2 = r^2 \qquad ①$$

If the equation ① is developed, the following equation ② can be obtained.

$$r = (h^2 + a^2)/2h \qquad ②$$

Figure 15B:
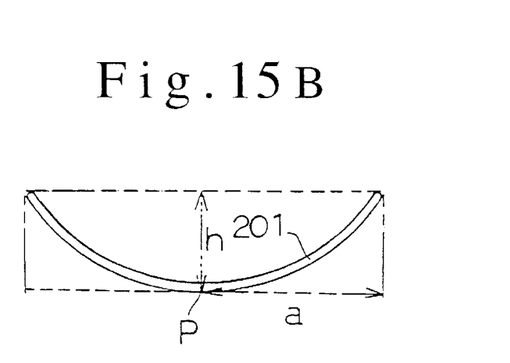

Thus, as shown in FIG. 15B, regarding the napkin as a whole as a circular arc A, a height h (distance from a point (p) of contact between the napkin and a table when the napkin was placed on the table such that opposite ends of the napkin become same in height to the opposite ends) of the erected portion of the napkin from a bottom surface of the napkin and a representing a half of an apparent length of the curved napkin were measured, and the h and the a were entered into the equation ② thereby obtaining a radius of curvature. Specifically, the sanitary napkin was placed under a stressless condition, and the height h from the longitudinal (widthwise direction) opposite ends to a lowermost point p was obtained. Also, a linear distance (2a) between the opposite end portions of the napkin was obtained to calculate a. The h and a thus obtained were entered into the above equation ② thereby obtaining the radius of curvature r of the sanitary napkin.

The width W2 of the left free edge portion 224 and the width W3 of the right free edge portion are preferably 5 to 30 mm, and the length L2 of the front free edge portion 226 and the length L3 of the rear free edge portion 223 are preferably 30 to 150 mm.

The sanitary napkin according to this embodiment can be used in the same manner as the generally known sanitary napkin for night use, or the like.

Since the sanitary napkin 201 according to this embodiment is constructed in the manner as mentioned above, since the front, rear, left, and right free edge portions 227, 223, 224, and 225 in the absorbent layer 202 are curved/moved in obedience to the motion of the body of the wearer so as to be nicely fitted to the body as shown in FIG. 11, irrespective of what kinds of shorts are in wear, for example, even in wear of a loose shorts and motion of the body of the weaer' body, a high fitness can be obtained and leakage hardly occurs.

The eighth embodiment according to the absorbent article of the present invention will be described hereinafter with reference to FIGS. 12 to 14.

Figure 12:
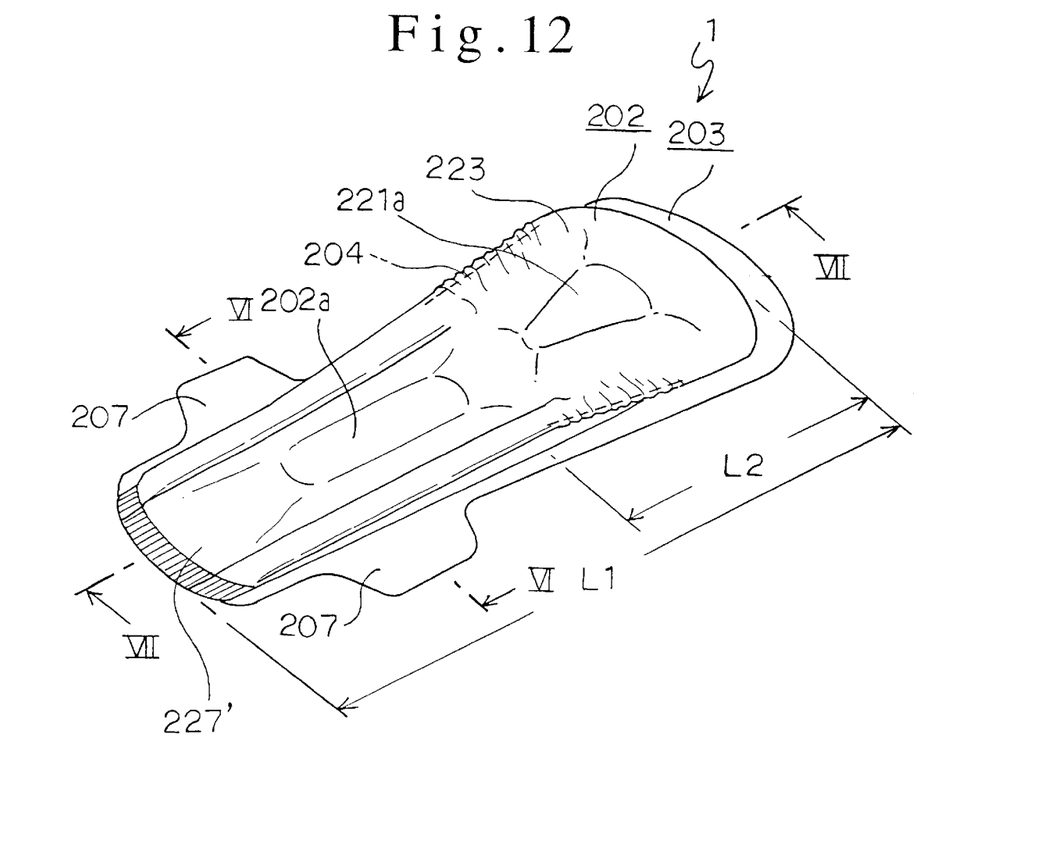
FIG. 12 is a perspective view showing a sanitary napkin as the eighth embodiment of an absorbent article of the present invention.
Figure 13:
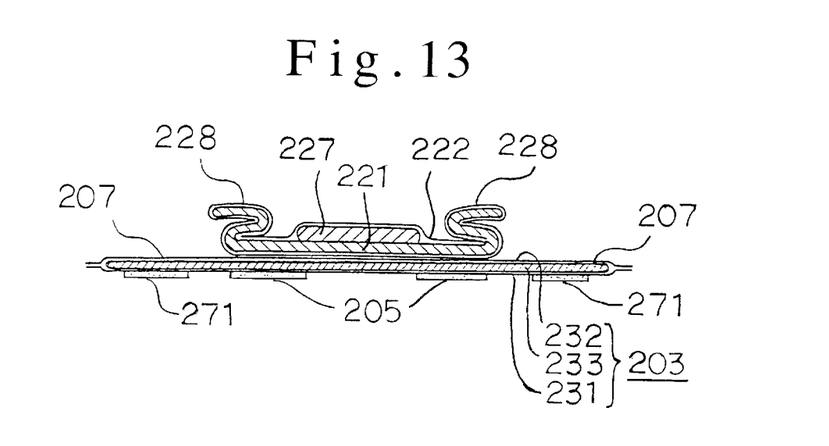
FIG. 13 is a sectional view taken in line VI—VI of the sanitary napkin shown in FIG. 12.
Figure 14:
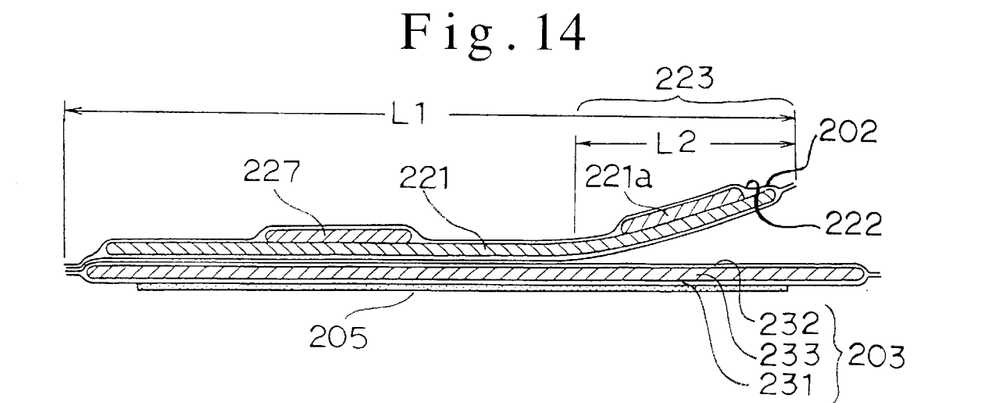
FIG. 14 is a sectional view taken on line VII—VII of the sanitary napkin shown in FIG. 12.

Here, FIG. 12 is a perspective view showing a sanitary napkin as the eighth embodiment of the absorbent article of the present invention, FIG. 13 is a sectional view taken on line VI—VI of the sanitary napkin shown in FIG. 12, and FIG. 14 is a sectional view taken on line VII—VII of the sanitary napkin shown in FIG. 12.

The points not particularly described in detail are the same as the first to seventh embodiments.

In a sanitary napkin 201 according to this embodiment shown in FIGS. 12 to 14, the absorbent layer 202 includes a liquid retentive absorbent member 221, and a liquid-permeable topsheet 222 provided in such a manner as to cover at least a skin contacting surface side of the absorbent member 221. The longitudinal central portion 202a of the absorbent layer 202 is fixed to the leakage-preventive layer 203, and a rear free edge portion 223, which is not fixed to the leakage-preventive layer 203, is formed thereon. An elastic member 204 is disposed on the rear free edge portion 223 over a predetermined length along the longitudinal direction of the absorbent member 221, so that the rear free edge portion 223 is erected upwardly of the leakage-preventive layer 203 by contraction of the elastic member 204.

More specifically, in the sanitary napkin 201 according to this embodiment is a so-called night-use sanitary napkin, in which the length of the sanitary napkin itself is long (length: 250 to 400 mm), and the rear portion (the portion located on the back side of the wearer when in wear) is widthwise enlarged in a sector-like configuration.

In the absorbent layer 202, that portion of the absorbent layer 202 which is fixed to the leakage-preventive layer 203, is defined as a central portion 202a and a front portion 227', and the rear free edge portion 223 is not fixed to the leakage-preventive layer 203 and thus erectable.

The rear free edge portion 223 is provided with a second absorbent member 221a such that a widthwise central portion of the rear free edge portion 223 is raised (to form a three-dimensional configuration). The second absorbent member 221a is disposed between the absorbent member 221 and the topsheet 222.

Elastic members 204 are arranged on opposite left and right side edge portions of the rear free edge portion 223 along the side edges of the absorbent member 221 and in such a manner as to be covered with the topsheet 222.

Adhesive agent is applied to the back surface side of the opposite left and right sides of a front part of the leakage-preventive layer 203 to thereby provide one pair of wing portions 27 each provided with a slip-preventive portion 271. In this embodiment, the wing portions 207 like other parts of the leakage-preventive layer 203 are formed of a liquid-permeable sheet 232, a leakage-preventive sheet 231, and an absorbent sheet 233 interposed therebetween. It is also acceptable that instead of providing the absorbent sheet 233, the liquid-permeable sheet 232 and the leakage-preventive sheet 231 are bonded together.

The length L1 of the absorbent layer 202 is preferably 230 to 400 mm, and the length L2 of the rear free edge portion 223 is preferably 50 to 200 mm. In other words, the rear free edge portion 223 refers to the part of the absorbent layer 2 which has a predetermined length from the rear end of the absorbent layer 2.

On the opposite left and right side edge portions of the absorbent layer 202 at the front portion 227' and the central portion 202a, the topsheet 222 and the absorbent member 221 are integrally folded in superimposed relation and leakage-preventive walls 228 are formed.

Also in the sanitary napkin thus constructed according to this embodiment, the same effects as the sanitary napkin according to the first and seven embodiments can be exhibited.

The sanitary napkin according to this embodiment can also be manufactured in the same manner as the sanitary napkin according to the seventh embodiment.

An absorbent article according to the present invention is not limited to the above embodiments, and many changes and modifications can be made without departing from the gist of the present invention.

For example, in the first embodiment, the leakage-preventive layer 3 made be formed of only the leakage-preventive sheet 32 (there is no need of a provision of the liquid-permeable sheet 31 and the absorptive portion 33).

The absorbent member 24 is not necessarily disposed over a widthwise entire area of the free edge portion 22. For example, it is acceptable that the elastic members 25 are provided on edge ends of the free edge portions 22, and the absorbent member 24 is present only up to a widthwise generally central portion of each free edge portion 22.

The elastic member 25 is not necessarily provided on the free end 22a only if the free edge portion 22 can be erected, and the member 25 may be disposed on a widthwise central portion of the free edge portion.

The fixed portion 21 may be fixed not only by adhesive agent but also by heat sealing, supersonic sealing, or the like. In the fixed portion 21, the bonding area (fixing area) between the absorbent layer 2 and the leakage-preventive layer 3 is, for example, the opposite left and right side edge portions and the longitudinal opposite end edges of the fixed portion 21 in the above-mentioned embodiments. However, the fixing area may be the entire surface of the fixed portion.

For example, in the eighth embodiment, the elastic members may be provided on the widthwise opposite left and right end portions of the absorbent article and the left and right free edge portions may be erected upwardly as in the seventh embodiment. It is also accepted that the second absorbent member 202a exhibits an elongate configuration extending to the rear portion, and the absorbent member is raised so that it fits nicely to the body of the wearer from the discharging portion to the groove portion of the hip.

In the eighth embodiment, the second absorbent member 221a is disposed between the absorbent member 221 and the topsheet 222. However, the second absorbent member 221a may be disposed between the adjacent layers of the absorbent member 221.

What is claimed is:

1. An absorbent article having a substantially elongate configuration, comprising a liquid-impermeable leakage-preventive layer, and a liquid-retentive absorbent layer disposed above said leakage-preventive layer, wherein said absorbent layer comprises a liquid-retentive absorbent member and a liquid-permeable topsheet, said absorbent layer defining a fixed portion and a pair of left and right free edge portions, said fixed portion being fixed to said leakage-preventive layer, said free edge portions being located on opposite left and right sides in the longitudinal direction of said fixed portion and being free from attachment with said leakage-preventive layer to form a free end, said absorbent member being present in both of said fixed portion and said pair of left and right free edge portions, and said free edge portions each having an elastic member arranged over a predetermined length along a longitudinal direction of said absorbent layer, said free edge portions being erected upwardly by contraction of said elastic members.

2. An absorbent article according to claim 1, wherein said topsheet is arranged in such a manner as to cover at least a skin contacting surface side of said absorbent member, said fixed portion is located on a widthwise central portion of said absorbent layer, and said free edge portions are continuously formed with opposite left and right side edges of said fixed portion, respectively.

3. An absorbent article according to claim 1, wherein a skin non-contacting surface of said absorbent article is provided with slip-preventive means for attaching said absorbent article to an undergarment when in use, and a portion of said absorbent article fixed by said slip-preventive means is larger in width than said fixed portion of said absorbent layer.

4. An absorbent article according to claim 1, wherein groove portions are each formed in opposite left and right side portions of said fixed portion.

5. An absorbent article according to claim 1, wherein said fixed portion and said free edge portions are separately formed, and said free edge portions are firmly secured at base end portions and/or intermediate portions thereof to opposite left and right side portions of said fixed portion.

6. An absorbent article according to claim 1, wherein said absorbent layer includes a rear free edge portion which is not fixed to said leakage-preventive layer, at least said rear free edge portion has an elastic member arranged over a predetermined length along a longitudinal direction of said absorbent layer, said rear free edge portions being erected upwardly by contraction of said elastic member.

7. The absorbent article according to claim 1, wherein said leakage-preventive layer includes a leakage-preventive sheet, a liquid permeable sheet, and an absorptive sheet located between the leakage-preventive sheet and the liquid permeable sheet.

8. The absorbent article according to claim 1, wherein said topsheet is a single continuous sheet extending at least from one of said free ends, through said fixed portion to the other of said free ends.

9. The absorbent article according to claim 1, wherein said absorbent member is a single member extending into said pair of left and right free edge portions from said fixed portion.

10. An absorbent article having a substantially elongate configuration, comprising a liquid-impermeable leakage-preventive layer, and a liquid retentive absorbent layer disposed above said leakage-preventive layer, said absorbent article being attached to an undergarment when in use, wherein said absorbent layer comprises a liquid-retentive absorbent member and a liquid-permeable topsheet, said absorbent layer defining a fixed portion and a pair of left and right free edge portions, said fixed portion being fixed to said leakage-preventive layer, said free edge portions being located on opposite left and right sides in the longitudinal direction of said fixed portion and being free from attachment with said leakage-preventive layer to form a free end, said absorbent member being present in both of said fixed portion and said pair of left and right free edge portions, and said free edge portions each having an elastic member arranged over a predetermined length along a longitudinal direction of said absorbent layer, said free edge portions being erected upwardly by contraction of said elastic members.

11. An absorbent article according to claim 10, wherein said topsheet is arranged in such a manner as to cover at least a skin contacting surface side of said absorbent member, said fixed portion is located on a widthwise central portion of said absorbent layer, and said free edge portions are continuously formed with opposite left and right side edges of said fixed portion, respectively.

12. An absorbent article according to claim 10, wherein a skin non-contacting surface of said absorbent article is provided with slip-preventive means for attaching said absorbent article to an undergarment when in use, and a portion of said absorbent article fixed by said slip-preventive means is larger in width than said fixed portion of said absorbent layer.

13. An absorbent article according to claim 10, wherein groove portions are each formed in opposite left and right side portions of said fixed portion.

14. An absorbent article according to claim 10, wherein said fixed portion and said free edge portions are separately formed, and said free edge portions are firmly secured at base end portions and/or intermediate portions thereof to opposite left and right side portions of said fixed portion.

15. An absorbent article according to claim 10, wherein said absorbent layer includes a rear free edge portion which is not fixed to said leakage-preventive layer, at least said rear free edge portion has an elastic member arranged over a predetermined length along a longitudinal direction of said absorbent layer, said rear free edge portion being erected upwardly by contraction of said elastic member.

16. The absorbent article according to claim 10, wherein said leakage-preventive layer includes a leakage-preventive sheet, a liquid permeable sheet, and an absorptive sheet located between the leakage-preventive sheet and the liquid permeable sheet.

17. The absorbent article according to claim 10, wherein said topsheet is a single continuous sheet extending at least from one of said free ends, through said fixed portion to the other of said free ends.

18. The absorbent article according to claim 10, wherein said absorbent member is a single member extending into said pair of left and right free edge portions from said fixed portion.

* * * * *